(12) United States Patent
McKnight

(10) Patent No.: US 8,966,812 B2
(45) Date of Patent: Mar. 3, 2015

(54) TRAP FOR BED BUGS AND THE LIKE

(75) Inventor: Susan McKnight, West Hartford, CT (US)

(73) Assignee: Susan McKnight, Inc., Memphis, TN (US)

( * ) Notice: Subject to any disclaimer, the term of this patent is extended or adjusted under 35 U.S.C. 154(b) by 614 days.

(21) Appl. No.: 12/327,856

(22) Filed: Dec. 4, 2008

(65) Prior Publication Data

US 2009/0145020 A1   Jun. 11, 2009

Related U.S. Application Data

(60) Provisional application No. 60/992,836, filed on Dec. 6, 2007.

(51) Int. Cl.
*A01M 1/10* (2006.01)
*A01M 1/02* (2006.01)
*A01N 37/36* (2006.01)

(52) U.S. Cl.
CPC ............... *A01M 1/023* (2013.01); *A01M 1/103* (2013.01); *A01N 37/36* (2013.01)
USPC .................................. 43/123; 43/107; 43/121

(58) Field of Classification Search
USPC .................. 43/123, 121, 107, 113; 119/61.53
See application file for complete search history.

(56) References Cited

U.S. PATENT DOCUMENTS

| | | | | |
|---|---|---|---|---|
| 109,282 A * | 11/1870 | Williams | ........................ | 43/121 |
| 140,954 A * | 7/1873 | Rubarth | ........................ | 43/121 |
| 280,291 A * | 6/1883 | Bunnell | ........................ | 43/121 |
| 400,460 A * | 4/1889 | Jennings | ........................ | 43/121 |
| 602,410 A * | 4/1898 | Selvidge | ........................ | 43/121 |
| 898,852 A * | 9/1908 | Duggan | ........................ | 43/109 |
| 1,024,767 A * | 4/1912 | Dempster | ........................ | 43/121 |
| 1,135,159 A * | 4/1915 | Cox | ........................ | 43/121 |
| 1,265,481 A * | 5/1918 | Mosby | ........................ | 43/121 |
| 1,471,986 A * | 10/1923 | Voges | ........................ | 43/121 |
| 1,515,094 A * | 11/1924 | Cumbie | ........................ | 43/121 |
| 1,521,323 A * | 12/1924 | Reeder | ........................ | 43/113 |
| 1,569,170 A * | 1/1926 | Braun et al. | ........................ | 43/121 |
| 1,614,157 A * | 1/1927 | Schneider | ........................ | 43/123 |

(Continued)

FOREIGN PATENT DOCUMENTS

DE   10108179 A1 *   9/2002   ............. A01M 1/02
EP   1745697 A1   1/2007

(Continued)

OTHER PUBLICATIONS

International Search Report for International Application No. PCT/US2008/013431 filed Dec. 5, 2008 (3 pages).

(Continued)

*Primary Examiner* — Darren W Ark
(74) *Attorney, Agent, or Firm* — McCormick, Paulding & Huber LLP

(57) ABSTRACT

A climb-up pitfall trap for attracting and capturing bed bugs and the like comprises a rough exterior surface, a precipice, a smooth interior surface and sensory lures. The sensory lures include heat, carbon dioxide and/or a lure composition. The lure composition comprises a combination of (a) L-lactic acid, and (b) a fatty acid from the group consisting of (1) propionic acid, (2) butyric acid, and (3) valeric acid. The lure composition may also comprise (c) octenol. A method for attracting and capturing bed bugs and the like uses the climb-up pitfall trap in a bed bug infested environment.

27 Claims, 5 Drawing Sheets

(56) References Cited

U.S. PATENT DOCUMENTS

| | | | |
|---|---|---|---|
| 1,621,318 A * | 3/1927 | Edwards et al. | 43/121 |
| 1,667,048 A * | 4/1928 | Rawlings | 43/121 |
| 1,772,989 A * | 8/1930 | Emley | 43/107 |
| 1,944,784 A * | 1/1934 | Cook | 43/123 |
| 1,971,367 A * | 8/1934 | Brooke | 43/107 |
| 2,162,502 A * | 6/1939 | Goulard | 43/107 |
| 2,167,978 A * | 8/1939 | Balthasar | 43/121 |
| 2,255,360 A * | 9/1941 | Miller | 43/121 |
| 2,345,408 A * | 3/1944 | Martin | 43/107 |
| 2,435,317 A * | 2/1948 | McGrew | 43/121 |
| 2,606,391 A * | 8/1952 | McGrew | 43/121 |
| 3,550,308 A * | 12/1970 | Ibach | 43/121 |
| 4,030,233 A * | 6/1977 | Wunsche | 43/121 |
| 4,223,012 A * | 9/1980 | Anderson et al. | 424/84 |
| 4,263,740 A * | 4/1981 | Hemsarth et al. | 43/121 |
| 4,328,637 A * | 5/1982 | Eichmuller et al. | 43/121 |
| 4,423,564 A * | 1/1984 | Davies et al. | 43/121 |
| 4,506,473 A * | 3/1985 | Waters, Jr. | 43/107 |
| 4,522,190 A * | 6/1985 | Kuhn et al. | 126/263.02 |
| 4,600,581 A * | 7/1986 | Aldrich | 424/84 |
| 4,608,774 A * | 9/1986 | Sherman | 43/121 |
| 4,698,934 A * | 10/1987 | Gonzalez et al. | 43/121 |
| 4,747,230 A * | 5/1988 | Zalesky | 43/121 |
| 4,803,954 A * | 2/1989 | Welch et al. | 119/61.53 |
| 4,818,526 A * | 4/1989 | Wilson et al. | 424/84 |
| 4,907,366 A * | 3/1990 | Balfour | 43/114 |
| 5,042,192 A * | 8/1991 | Osteen | 43/109 |
| 5,069,166 A * | 12/1991 | Ahuna | 119/61.53 |
| 5,090,153 A * | 2/1992 | Mullen et al. | 43/121 |
| 5,189,830 A * | 3/1993 | Montemurro | 43/121 |
| 5,193,302 A * | 3/1993 | Rusco et al. | 43/121 |
| 5,205,064 A * | 4/1993 | Nolen | 43/112 |
| D335,940 S * | 5/1993 | McGrath et al. | D30/130 |
| 5,253,450 A * | 10/1993 | Muramatsu | 43/121 |
| 5,253,609 A * | 10/1993 | Partelow et al. | 119/61.53 |
| 5,258,176 A * | 11/1993 | Keenan | 424/84 |
| 5,277,149 A * | 1/1994 | East | 119/61.53 |
| 5,339,563 A * | 8/1994 | Job | 43/107 |
| 5,382,422 A * | 1/1995 | Dieguez et al. | 43/111 |
| 5,392,559 A * | 2/1995 | Long | 43/121 |
| 5,414,954 A * | 5/1995 | Long | 43/121 |
| 5,560,315 A * | 10/1996 | Lampe | 119/61.53 |
| 5,561,941 A * | 10/1996 | Long | 43/121 |
| 5,566,500 A * | 10/1996 | Long | 43/121 |
| 5,577,461 A * | 11/1996 | Sebastian et al. | 119/61.53 |
| 5,657,575 A * | 8/1997 | Miller et al. | 43/121 |
| 5,657,576 A * | 8/1997 | Nicosia | 43/107 |
| 5,771,628 A * | 6/1998 | Nobbs | 43/121 |
| 5,799,436 A * | 9/1998 | Nolen et al. | 43/112 |
| 5,855,185 A * | 1/1999 | Scott | 119/61.53 |
| 5,900,244 A * | 5/1999 | Howse | 424/405 |
| 5,926,999 A * | 7/1999 | Vernon et al. | 43/121 |
| 5,979,360 A * | 11/1999 | Tharp | 119/61.53 |
| 5,996,531 A * | 12/1999 | Anderson | 119/61.53 |
| 6,055,766 A * | 5/2000 | Nolen et al. | 43/112 |
| 6,106,821 A * | 8/2000 | Baker et al. | 424/84 |
| 6,145,243 A * | 11/2000 | Wigton et al. | 43/107 |
| 6,199,316 B1 * | 3/2001 | Coventry | 43/107 |
| 6,305,122 B1 * | 10/2001 | Iwao et al. | 43/121 |
| 6,327,810 B1 * | 12/2001 | Howse | 43/121 |
| 6,505,433 B2 * | 1/2003 | Roberts | 43/109 |
| 6,510,648 B2 * | 1/2003 | Roberts | 43/109 |
| 6,513,280 B2 * | 2/2003 | Roberts | 43/109 |
| 6,516,559 B1 * | 2/2003 | Simchoni et al. | 43/121 |
| 6,593,299 B1 * | 7/2003 | Bennett et al. | 514/18 |
| 6,718,687 B2 * | 4/2004 | Robison | 43/114 |
| 6,790,436 B2 * | 9/2004 | Williams et al. | 424/76.3 |
| 6,800,279 B2 * | 10/2004 | Bernier et al. | 424/84 |
| 6,860,062 B2 * | 3/2005 | Spragins | 43/121 |
| 6,866,858 B2 * | 3/2005 | Nolen et al. | 424/406 |
| 6,898,896 B1 * | 5/2005 | McBride et al. | 43/107 |
| 6,920,716 B2 * | 7/2005 | Kollars et al. | 43/107 |
| 7,074,830 B2 * | 7/2006 | Durand et al. | 43/107 |
| 7,117,632 B2 * | 10/2006 | Lin | 43/107 |
| 7,171,778 B1 * | 2/2007 | Thompson, III | 43/121 |
| 7,243,458 B2 * | 7/2007 | Miller et al. | 43/113 |
| 7,299,587 B1 * | 11/2007 | Metcalfe | 43/121 |
| 7,343,710 B2 * | 3/2008 | Metcalfe | 43/121 |
| 7,591,099 B2 * | 9/2009 | Lang et al. | 43/107 |
| D668,314 S * | 10/2012 | MacKay et al. | D22/122 |
| 8,402,690 B2 * | 3/2013 | Schneidmiller et al. | 43/123 |
| 8,635,807 B2 * | 1/2014 | Frisch et al. | 43/123 |
| 8,677,679 B2 * | 3/2014 | Black et al. | 43/123 |
| 2002/0112396 A1 * | 8/2002 | Nyberg | 43/121 |
| 2004/0025412 A1 * | 2/2004 | Simchoni et al. | 43/107 |
| 2005/0138858 A1 * | 6/2005 | Lyng | 43/121 |
| 2006/0150473 A1 * | 7/2006 | Bette | 43/107 |
| 2007/0044372 A1 | 3/2007 | Lang | |
| 2008/0017775 A1 * | 1/2008 | Gary | 248/346.11 |
| 2008/0072830 A1 * | 3/2008 | Wrigge | 119/61.53 |
| 2009/0056633 A1 * | 3/2009 | McDaniel et al. | 119/61.53 |
| 2009/0145019 A1 * | 6/2009 | Nolen et al. | 43/121 |
| 2009/0145020 A1 * | 6/2009 | McKnight | 43/123 |
| 2009/0223115 A1 * | 9/2009 | Lang et al. | 43/123 |
| 2009/0229528 A1 * | 9/2009 | McMurtry | 119/61.53 |
| 2009/0260276 A1 * | 10/2009 | Kirsch et al. | 43/123 |
| 2009/0282728 A1 * | 11/2009 | McKnight et al. | 43/123 |
| 2010/0212213 A1 * | 8/2010 | Hope et al. | 43/123 |
| 2010/0223837 A1 * | 9/2010 | Borth et al. | 43/123 |
| 2011/0041385 A1 * | 2/2011 | Faham et al. | 43/123 |
| 2011/0047860 A1 * | 3/2011 | Black et al. | 43/123 |
| 2011/0072712 A1 * | 3/2011 | Black et al. | 43/123 |
| 2011/0138678 A1 * | 6/2011 | Smith | 43/107 |
| 2011/0209665 A1 * | 9/2011 | Rizk et al. | 119/61.53 |
| 2011/0225873 A1 * | 9/2011 | McKnight et al. | 43/123 |
| 2012/0204477 A1 * | 8/2012 | Fairleigh et al. | 43/121 |
| 2012/0246998 A1 * | 10/2012 | Vasudeva et al. | 43/123 |
| 2013/0047495 A1 * | 2/2013 | Frisch | 43/123 |
| 2013/0180161 A1 * | 7/2013 | Vasudeva et al. | 43/123 |
| 2013/0180162 A1 * | 7/2013 | Vasudeva et al. | 43/123 |
| 2013/0219771 A1 * | 8/2013 | Black et al. | 43/123 |
| 2013/0318861 A1 * | 12/2013 | Roeder | 43/123 |
| 2014/0075825 A1 * | 3/2014 | Vasudeva et al. | 43/123 |
| 2014/0250766 A1 * | 9/2014 | Singh et al. | 43/121 |
| 2014/0311016 A1 * | 10/2014 | Wang et al. | 43/123 |

FOREIGN PATENT DOCUMENTS

| | | | | |
|---|---|---|---|---|
| GB | 2463953 A * | 4/2010 | | A01M 1/02 |
| JP | 07203821 A * | 8/1995 | | A01M 1/02 |
| JP | 08154553 A * | 6/1996 | | A01M 1/10 |
| JP | 08256658 A | 10/1996 | | |
| JP | 10229801 A * | 9/1998 | | A01M 1/02 |
| JP | 11346628 A * | 12/1999 | | A01M 1/02 |
| JP | 11346629 A * | 12/1999 | | A01M 1/02 |
| JP | 2000139318 A * | 5/2000 | | A01M 1/02 |
| JP | 2003061541 A * | 3/2003 | | A01M 1/02 |
| JP | 2005065631 A * | 3/2005 | | A01M 1/02 |
| JP | 59062504 | 1/2007 | | |
| JP | 2007074908 A * | 3/2007 | | A01M 1/02 |
| WO | 9826661 A1 | 6/1998 | | |
| WO | WO9926471 A1 | 6/1999 | | |
| WO | WO2005120224 A1 | 12/2005 | | |

OTHER PUBLICATIONS

Written Opinion of the International Searching Authority for International Application No. PCT/US2008/013431 filed Dec. 5, 2008 (5 pages).

Aboul-Nasr, A.E.; Erakey, M.A.S., "Behavior and Sensory Physiology of the Bed-Bug, *Cimex lectularius* L., to Some Environmental Factors: Chemoreception", Bull. Soc. Entomol. Egypte., 1968, pp. 353-362, vol. 52.

Aboul-Nasr, A.E.; Erakey, M.A.S., "The Effect of Contact and Gravity Reactions Upon the Bed-bug, *Cimex lectularius* L.", Bull. Soc. Entomol. Egypte., 1968, pp. 363-370, vol. 52.

Aboul-Nasr, A.E.; Erakey, M.A.S., "On the Behavior and Sensory Physiology of the Bed-bug", Bull. Soc. Entomol. Egypte., 1967, pp. 43-54, vol. 51.

Busvine, James, "Insects and Hygiene: The Biology and Control of Insect Pests of Medical and Domestic Importance in Britain", 1951, pp. 221-232, Methuen & Co. Ltd., London.

(56) References Cited

OTHER PUBLICATIONS

Cwilich, R.; Nier, GG; Meron, AV; "Bedbugs Resistant to Gamma BHC (lindane) in Isreal", Nature, Mar. 23, 1957, p. 636, vol. 179.
Doggett, Stephen, "A Code of Practice for the Control of Bed Bug Infestations in Australia (Draft)", Australian Environmental Pest Managers Association, Oct. 20, 2005, pp. 1-47.
Doggett, Stephen L.; Geary, Merilyn J.; Russell, Richard C. "Encasing Mattresses in Black Plastic Will Not Provide Thermal Control of Bed Bugs, Cimex spp. (Hemiptera: Cimicidae)", J. Econ. Entomol., 2006, pp. 2132-2135, vol. 99, No. 6, Entomological Society of America.
Fletcher, M.G.; Axtell, R.C. "Susceptibility of the Bedbug, Cimex lectularius, to Selected Insecticides and Various Treated Surfaces", Medical and Veterinary Entomology, 1993, pp. 69-72, vol. 7.
Hartnack, Hugo "Unbidden House Guests", 1943, pp. 60-62, Hartnack Publishing Co., Tacoma, Wash.
Hebert, Michael "Get the Roll Surface Right", Plastics Technology (www.PTOnline.com), 2007, Gardner Publications, Inc.
Lehane, M.J. "The Biology of Blood-Sucking in Insects", 2004, pp. 32-43, 2nd Edition, Cambridge University Press.
Lofgren, C.S.; Keller, J.C.; Burden, G.S. "Resistance Tests with the Bed Bug and Evaluation of Inscecticides for Its Control", Journal of Economic Entomology, Apr. 1958, pp. 241-244, vol. 51, No. 2, Entomological Society of America.
Mallis, Arnold "Handbook of Pest Control: The Behavior, Life History, and Control of Household Pests", 1960, pp. 392-418, Third Edition, MacNair-Dorland Co., New York.
Marshall, Adrian G., "The Ecology of Ectoparasitic Insects",1981, pp. 165-203, Academic Press, New York.
Marx, Ruth "Ober Die Wirtsfindung Und Die Bedeutung Des Artspezifischen Duftstoffes Bei Cimex lectularius Linne", 1954, pp. 40-72.
Mellanby, Kenneth "The Physiology and Activity of the Bed-bug (Cimex lectularius L.) in a Natural Infestation", Parasitol, 1939, pp. 200-211, vol. 31.
Moore, David J.; Miller, Dini M. "Laboratory Evaluations of Insecticide Product Efficacy for Control of Cimex lectularius", Journal of Economic Entomology, 2006, pp. 2080-2086, vol. 99, No. 6, Entomological Society of America.
Murlis, John; Elkinton, Joseph S.; Carde, Ring T. "Odor Plumes and How Insects Use Them", Annu. Rev. Entomol, 1992, pp. 505-532, vol. 37, Annual Reviews Inc.
Overal, W.L.; Wingate, L.R. "The Biology of the Batbug Stricticimex antennatus (Hemiptera: Cimicidae) in South Africa", Ann. Natal. Mus., 1976, pp. 821-828, vol. 23(3).
Panagiotakopulu, Eva; Buckland, Paul C. "Cimex lectularius L., the Common Bed Bug from Pharaonic Egypt", 1999, Antiquity Publications, Ltd.
Quarles, William "Bed Bugs Bounce Back", The IPM Practitioner: Monitoring the Field of Pest Management, Mar./Apr. 2007, pp. 1-8, vol. XXIX, No. 3/4.
Rivnay, Ezekiel "Studies in Tropisms of the Bed Bug Cimex lectularius L.", Parasitology, 1932, pp. 121-136, vol. 24.
Romero, Alvaro; Potter, Michael F.; Potter, Daniel A.; Haynes, Kenneth F. "Insecticide Resistance in the Bed Bug: A Factor in the Pest's Sudden Resurgence?", Journal of Medical Entomology, 2007, pp. 175-178, vol. 44(2).
Schofield, Steven W.; Sutcliffe, James F. "Human Individuals Vary in Attractiveness for Host-Seeking Black Flies (Diptera: Simuliidae) Based on Exhaled Carbon Dioxide", Journal of Medical Entomology, 1996, pp. 102-108, vol. 33, No. 1.
Sutcliffe, James F. "Distance Orientation of Biting Flies to Their Hosts", Insect Sci Applic., 1987, pp. 611-616, vol. 8, Nos. 4:5:6, ICIPE Science Press.
Usinger, Robert L. "Monograph of Cimicidae (Hemiptera-Heteroptera)", 1966, pp. 16-49, vol. VII, The Thomas Say Foundation.
Wainwright, S.A.; Biggs, W.D.; Currey, J.D.; Gosline, J.M. "Mechanical Design in Organisms", 1976, 100-101, A Halsted Press Book, John Wiley & Sons, New York.
Wright, Lawrence "Warm & Snug: The History of the Bed", 1962, pp. 131-134, pp. 165-167, Sutton Publishing.
Barrozo, RB; Lazzari, CR. 2004a. "The Response of the Booldsucking Bug Triatoma infestans to Carbon Dioxide and other Host Odours". Chem. Senses. 29:319-329.
Barrozo, RB; Lazzari, CR. 2004b. "Orientation Behaviour of the Blood-sucking Bug Triatoma infestans to Short-chain Fatty Acids: Synergistic Effect of L-Lactic Acid and Carbon Dioxide". Chem. Senses. 29:833-841.
BioSensory.com, NightWatch, http://www.biosensory.com/nightwatch.html (last visited Sep. 30, 2008).
Bosch, OJ; Geier, M; Boeckh, J. 2000. "Contribution of Fatty Acids to Olfactory Host Finding of Female Aedes aegypti". Chem. Senses 25:323-330.
Bosch, OJ; Geier, M; Boeckh, J. 1999. "Ammonia as an Attractive Component of Host Odour for the Yellow Fever Mosquito, Aedes aegypti". Chem. Senses 24:647-653.
Miller, DM "Your Bed Bug Questions Answered" http://www.msnbc.com/id/12133597 (last visited on Sep. 30, 2008).
Munoz, SS; "New Tactic Take a Bite Out of Bedbugs", The Wall Street Journal, Mar. 20, 2008, pp. 1-3.
Reinhardt, M; Siva-Jothy, M; 2007. "Biology of the Bed Bugs (Cimicidae)". Annu. Rev. Entomol. 52:351-374.
Smallegange, R; Qiu, YT; Van Loon, JJ; Takken, W. "Synergism between ammonia, lactic acid adn carboxylic acids as kairomones in teh host-seeking behaviour of the malaria mosquito Anopheles gambiae sensu stricto (Diptera: Culcidae)". Chem. Senses 30:145-152.
Bennett, GW; Wang, C; Mcgraw, G.; El-Nour, MA. "Traps and Attractants for Monitoring Bed Bug Infestations" S. McKnight, Biosensory, Inc.
An Office Action issued in corresponding Canadian Appln. No. 2,723,624 dated Jun. 13, 2012 (3 pages).
An Office Action issued in corresponding Canadian Appln. No. 2,707,490 dated Jul. 9, 2012 (2 pages).

* cited by examiner

TRAP FOR BED BUGS AND THE LIKE

PRIORITY CLAIM

This application claims the benefit of the U.S. Provisional patent application No. 60/992,836 filed on Dec. 6, 2007, the entirety of which is hereby incorporated by reference.

FIELD OF THE INVENTION

The invention relates to an insect removal trap and more particularly to a trap for bed bugs and the like having a climb-up pitfall trap and sensory lures (e.g. heat, carbon dioxide and/or a chemical lure).

BACKGROUND OF THE INVENTION

The trap of the present invention provides a more effective approach to attracting and capturing blood-sucking insects, particularly bed bugs. It combines a number of collection techniques with improved efficacy due to a synergistic combination of elements. It also reduces the amount of sprayed or broadcast chemicals that are used because ubiquitous non-toxic agents boost the effect of small amounts of chemicals.

The bed bug, *cimex lectularius*, is a small crawling blood-sucking insect that feeds on human, bird and bat blood. In the 1940s and 1950s, the widespread use of DDT and other residual pesticides caused a drastic decline in the bed bug population. However, bed bugs have developed resistances to these chemicals and are a rising threat to the commercial health of resort hotels, apartments, college dormitories, cruise ships and airplanes.

One approach to capturing insects has been the use of pitfall traps. The essential components of a pitfall trap are a container or pit and an interior wall that cannot be climbed. For example, a bug that falls into the trap will be unable to escape because it cannot climb up the interior wall, and is captured. Rough surfaces are easily climbed by bed bugs. Using their hook-like tarsal claws to engage fibres and surface roughness, bed bugs are capable of navigating vertical surfaces, for example, the underside of beds and even the human body. In fact, bed bugs exhibit behavior that seems to favor climbing inclined surfaces. In contrast, smooth surfaces can prove insurmountable and may even repel bed bugs. Smooth, hard surfaces can be made from glass, ceramics, metals, finished treatments on polished wood, finished treatments on paper, plastics and polymers. Insect and arthropod pitfall traps are known in the art, for example, U.S. Pat. No. 6,860,062 to Spragins discloses an adapted outdoor pitfall trap for crawling and flying insects; and U.S. Pat. No. 4,608,774 to Sherman discloses an indoor pitfall trap for cockroaches.

Another approach to capturing insects is the use of sensory lures. One such sensory lure is heat. Bed bugs are attracted to heat since heat can indicate a warm-blooded body. A temperature in the range of 43 to 45 degrees Celsius (109.4 to 113 degrees Fahrenheit) will attract bed bugs up to a distance of 25 mm at which point the bed bug will change path. Whereas a temperature of around 50 degrees Celsius (122 degrees Fahrenheit) will attract bed bugs to make direct contact with the heat source, and then be repelled after making contact. Insect and arthropod heat lures are known in the art, for example, U.S. Pat. No. 5,657,576 to Nicosia, U.S. Pat. No. 5,799,436 to Nolen, U.S. Pat. No. 6,055,766 to Nolen, U.S. Pat. No. 6,516,559 to Simchoni, and U.S. Pat. No. 7,117,632 to Lin each disclose the use of simulated human body heat to attract mosquitoes; U.S. Pat. No. 5,258,176 to Keenan discloses the use of heat to attract fleas and ticks; and published U.S. Patent Application No. 2007/0044372 to Lang discloses the use heat in the range of 26.6 to 37.7 degrees Celsius (80 to 100 degrees Fahrenheit) to attract bed bugs.

Another sensory lure is a chemical attractant. Bed bugs are attracted to chemical signals emitted by the hosts upon which they feed. Such chemical signals take the form of odor molecules, which drift away from the source by diffusion and by being carried in an air flow.

One chemical attractant is carbon dioxide, which is given off by respiring animals. Carbon dioxide is a ubiquitous gas in the atmosphere, with normal ambient background outdoor levels of 300 to 400 p.p.m. For example, normal adult human respiration expires around 200 ml/min of carbon dioxide, at a concentration of 45,000 p.p.m. in the expired air. Insects and arthropods that feed on host organisms are sometimes attracted to the increased carbon dioxide levels that are created by and thus surround the host. For example, tsetse flies and yellow fever mosquitoes are attracted by increased carbon dioxide levels over the ambient environment; blood-sucking conenose bugs are attracted by carbon dioxide levels between 300 and 400 p.p.m. over ambient levels; and mosquitoes are attracted linearly by carbon dioxide release rates up to 1,000 ml/min. Bed bugs are likewise attracted by carbon dioxide levels above ambient level.

Another chemical attractant detected by the olfactory senses of insects is an odor molecule such as L-lactic acid. L-lactic acid is a volatile component of human sweat that ranges in concentration from 0.5 to 5.0 mg/l. In some blood-sucking arthropods, L-lactic acid, when presented as a single stimulus, has only a slight or non-attractive effect. But when presented with carbon dioxide, L-lactic acid acts as a synergist and increases the attractiveness of the gas. The use of lactic acid as an attractant is known in the art, for example, U.S. Pat. No. 4,907,366 to Balfour discloses a trap for attracting mosquitoes using a composition consisting of lactic acid, carbon dioxide, water and heat.

Other chemical attractant odor molecules are the group of chemicals known as fatty acids, and, in particular, short chain fatty acids. Fatty acids are a volatile compound that include, but are not limited to, compounds such as acetic, propionic, isobutyric, butyric, isovaleric and valeric acids, all of which are present in human waste. The use of fatty acids as an attractant is known in the art, for example, Japan Patent No. JP-A-59062504 to Yasushi discloses an attractant composition for non-bloodsucking onion flies consisting of propionic acid, n-butyric acid, isobutyric acid, n-valeric acid, isovaleric acid, isocaprionic acid and 2-phenylethanol. See, also, U.S. Pat. No. 4,818,526 to Wilson and U.S. Pat. No. 5,258,176 to Keenan.

Another such attractant odor molecule is 1-Octen-3-ol (octenol). Octenol is a volatile component of cattle and human breath and sweat. Octenol is a potent olfactory attractant for tsetse flies and some mosquito species when combined with increased levels of carbon dioxide; for blood-sucking conenose bugs even at ambient carbon dioxide levels; and for mosquitoes, some of which are synergistically attracted by octenol and increased levels of carbon dioxide together. Others are attracted by octenol at ambient carbon dioxide levels. Bed bugs are attracted by octenol, but octenol is not an essential element in attracting bed bugs as evidenced by the fact that octenol is not emitted by birds, one of the other hosts of bed bugs. The use of carbon dioxide and/or octenol as an attractant of mosquitoes, no-see-ums, biting flies and ticks is known in the art from, for example, U.S. Pat. No. 5,205,064 to Nolen, U.S. Pat. No. 5,382,422 to Dieguez, U.S. Pat. No. 5,799,436 to Nolen, U.S. Pat. No. 6,055,766 to Nolen, U.S. Pat. No. 6,145,243 to Wigton, U.S. Pat. No. 6,199,316 to Coventry, U.S. Pat. No. 6,305,122 to Iwao, U.S. Pat. No. 6,516,559 to Simchoni, published U.S. Patent Application No. 2004/0025412 to Simchoni, U.S. Pat. No. 6,718,687 to Robison, U.S. Pat. No. 6,898,896 to McBride, U.S. Pat. No. 7,074,830 to Durand, U.S. Pat. No. 7,243,458 to Miller, U.S. Pat. No. 5,189,830 to Montemurro, and European Patent No. 1745697 to Geier.

Attractant chemical odor molecules can take on many forms and combinations. See, for example, European Patent No. WO 9826661 to Justus, U.S. Pat. No. 5,900,244 to Howes, U.S. Pat. No. 6,106,821 to Baker, U.S. Pat. No. 6,593,299 to Bennett, U.S. Pat. No. 6,800,279 to Bernier, U.S. Pat. No. 6,866,858 to Nolen, and U.S. Pat. No. 6,920,716 to Kollars.

Insect response to olfactory sensory neuron stimulation is dose dependent. For instance, the same compound may repel at one concentration and attract at another concentration.

The combination of highly effective chemical attractants with efficient traps allows for an improved control method to be developed. However, as is clear form the diversity of prior art, it is not possible to predict which compounds at which dosage levels will be effective attractants of a particular insect species. Accordingly, an effective trap for capturing bed bugs and the like, a lure composition for attracting bed bugs and the like, and a method for attracting and capturing bed bugs and the like is herein disclosed.

SUMMARY OF THE INVENTION

In accordance with the present invention, there is provided a novel trap, lure composition, lure arrangement, and method for attracting and capturing bed bugs and the like.

In accordance with one aspect of the invention, a climb-up pitfall trap for bed bugs and the like is provided. The trap comprises a rough exterior surface serving as an upward climbing wall. A precipice lines the inside edge of the exterior surface. A smooth interior surface is connected to the precipice and slopes downward from the precipice. A heat source and a carbon dioxide source are provided within an area surrounded by the interior surface. In addition, a lure composition may be provided.

In accordance with a second aspect of the invention, a lure composition for attracting bed bugs and the like is provided. The lure composition comprises a combination of (a) L-lactic acid, and (b) a fatty acid selected from the group consisting of: (1) propionic acid, (2) butyric acid, and (3) valeric acid.

In accordance with a third aspect of the invention, a lure arrangement for attracting bed bugs and the like is provided. The lure arrangement comprises a heat source, a carbon dioxide source, and a lure composition. The lure composition comprises a combination of (a) L-lactic acid, and (b) a fatty acid selected from the group consisting of: (1) propionic acid, (2) butyric acid, and (3) valeric acid.

In accordance with a fourth aspect of the invention, a method for attracting and capturing bed bugs and the like is provided. The method comprises positioning a climb-up pitfall trap in an infested environment. Then, providing the climb-up pitfall trap with a heat source, a carbon dioxide source and a lure composition. And then, activating the trap to expose the environment to heat from the heat source, carbon dioxide from the carbon dioxide source and gaseous vapors from the lure composition.

BRIEF DESCRIPTION OF THE FIGURES

Some aspects of the invention may take physical form in certain parts and arrangements, a preferred embodiment of which will be described in detail in the specification and illustrated in the accompanying drawings.

DETAILED DESCRIPTION OF THE PREFERRED EMBODIMENTS

Figure 1:
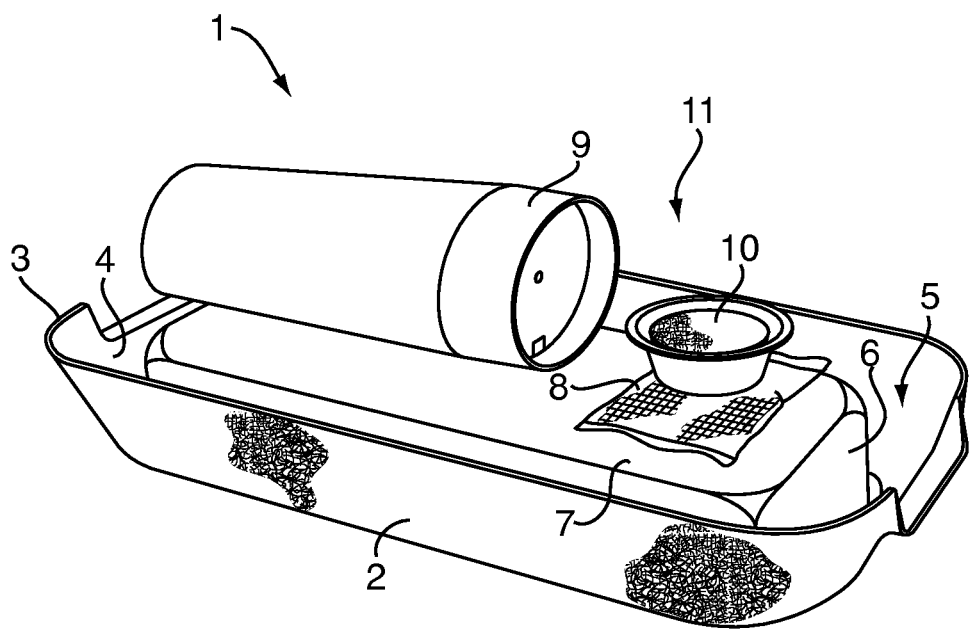
FIG. 1 is a perspective view of the climb-up pitfall trap of the present invention.
Figure 2:
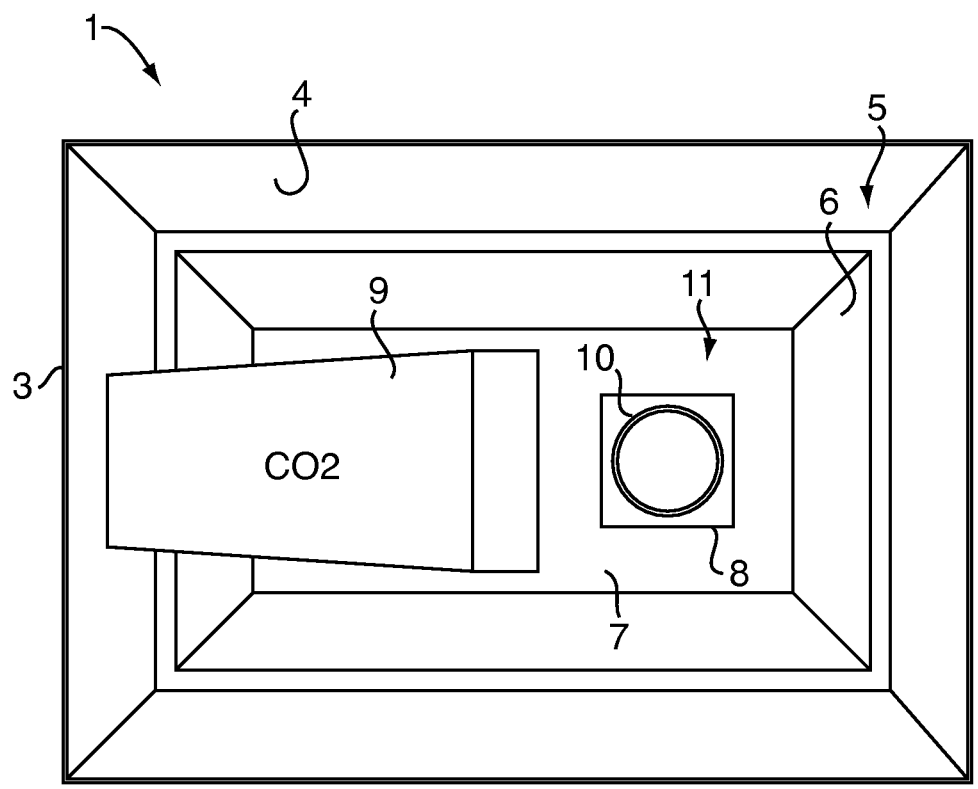
FIG. 2 is a top plan view of the climb-up pitfall trap in FIG. 1, in schematic form.

Referring to FIGS. 1-4, a climb-up pitfall bed bug trap 1 for attracting and capturing bed bugs is presented. The trap 1 is comprised of a rough exterior surface 2 that makes contact with the surrounding environment, such as a floor or a counter surface. The surface provides an upward sloping climbing wall that enables bed bugs to reach the pitfall precipice 3 at the top of the surface 2. The precipice 3 is a narrow surface that connects the exterior surface 2 to a smooth, slippery interior surface 4. The smooth interior surface 4 slopes down from the precipice 3 into a receptacle 5.

The receptacle 5 is defined by the interior surface 4 and a smooth, sloped retaining surface 6. The smooth retaining surface 6 extends upward to a center stage 7. The center stage 7 provides a supporting surface for sensory attractants and lures mounted or placed thereon.

It should be appreciated that a pitfall trap 1 that is not provided with a retaining wall 6 or a center stage 7 may still be provided with attractants and lures by placing the sensory attractants and lures in the environment enclosed within the interior surface 4.

The pitfall trap 1 is provided with sensory attractants and lures on the center stage 7, such as a heat source 8 and a carbon dioxide source 9. The heat source 8 and the carbon dioxide source 9 generate or emit heat and carbon dioxide, respectively, both of which mimic a human body to attract bed bugs and the like. In addition, the trap 1 may be provided with a lure composition 10. The lure composition 10 evaporates or emits an air born chemical composition specifically formulated to attract bed bugs and the like. Preferably, the heat source 8, the carbon dioxide source 9 and the chemical composition 10 are all placed proximate one another so that the emissions of each drift in approximately equal proportion and direction throughout the environment.

Figure 3:
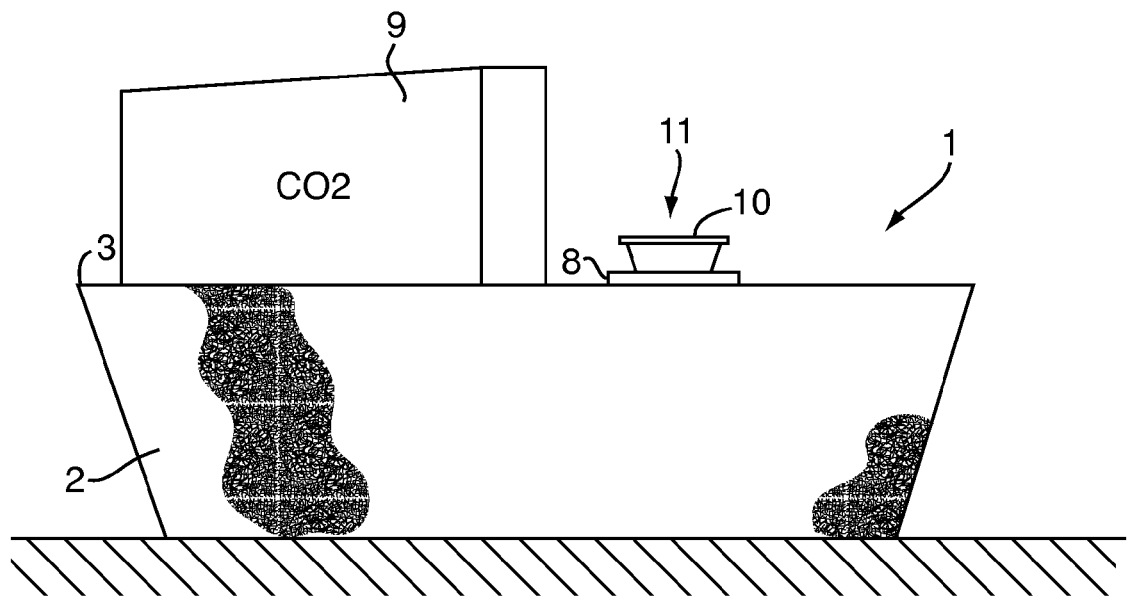
FIG. 3 is a side view of the climb-up pitfall trap in FIG. 2.
Figure 4:
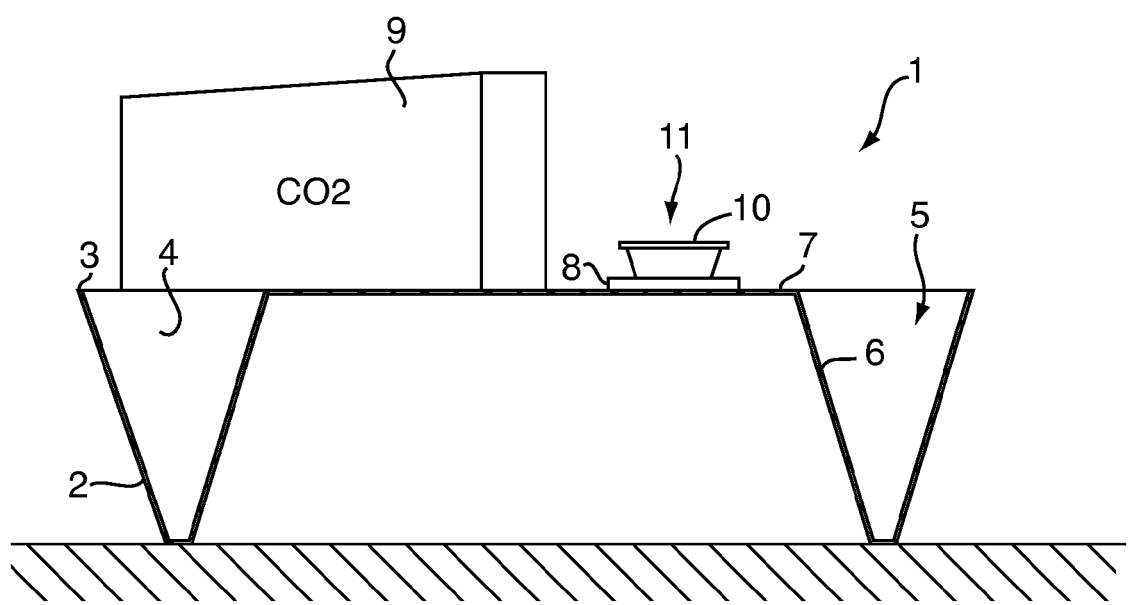
FIG. 4 is a side view of the climb-up pitfall trap in FIG. 2 in cross section

Referring to FIG. 1, the exterior surface 2 is, preferably, a four-sided structure that is rough as indicated by the textured surface panels in FIG. 1. Referring to FIGS. 3-4, for example, the exterior surface 2 is an inverted trapezoidal structure having a sloping surface that is 70 mm tall and 70 mm wide. However, the exterior surface 2 may slope at a more acute angle, be vertical, or slope at an obtuse angle. The exterior surface may be polygonal or rounded at the corners, as shown in FIG. 1. There is no required shape for the exterior surface 2 because the exterior surface 2 acts to engage the trap 1 with the surrounding environment and, thus, could be designed to fit many environments. The exterior surface 2 is rough and provides enough traction for bed bugs to engage the surface with their hooked tarsal claws. Surface roughness in excess of 300 microinch is sufficient to provide adequate traction. Such surface roughness may be achieved by making the exterior surface 2 from a material having surface roughness in excess of 300 microinch or by coating or covering the exterior surface 2 with such a material. For example, the exterior surface 2 may be made from unfinished wood or roughed plastic. Alternatively, the exterior surface 2 may be coated with fabric, paper or course abrasive.

The precipice 3 is, preferably, a smooth narrow edge less than 2 mm wide. The precipice 3 can be made from, covered by or coated by any smooth material. For example, the precipice 3 may be made from smooth materials including high-density polyethylene, polypropylene or glass.

Preferably, the interior surface 4 is a smooth downward-sloping four-sided structure. Referring to FIG. 3, the interior surface 4 can be formed from the under-side of the exterior surface 2. However, the interior surface 4 may be formed separately from the exterior surface 2 and the interior surface 4 may slope at an acute angle, be vertical or slope at an obtuse angle. The interior surface 4 may be polygonal or rounded. The only requirement placed on the shape of the interior surface 4 is that the slope be sufficiently vertical to cause a bed bug to slip thus creating a pitfall. The requirement placed on the slope of the interior surface 4 is interrelated with the smoothness/roughness of the interior surface 4. For example, an interior surface 4 having surface roughness less than 100 microinch is sufficient to prevent a bed bug from gaining traction with a substantially vertical interior surface 4. The interior surface 4 may be made, for example, from smooth materials including high-density polyethylene, polypropylene or glass.

Preferably, the retaining surface 6 is substantially vertical and smooth. However, the retaining surface 6 may slope at an acute angle, be vertical or slope at an obtuse angle. The retaining surface 6 may be polygonal or rounded. The only requirement placed on the shape of the retaining surface 6 is that the slope be sufficiently vertical to cause a bed bug to slip and, thus, confine the bed bug to the receptacle 5. The requirement placed on the slope of the retaining surface 6 is therefore interrelated with the smoothness/roughness of the retaining surface 6. A retaining surface 6 having surface roughness less than 100 microinch is sufficient to prevent a bed bug from gaining traction with a substantially vertical retaining surface 6. For example, the retaining surface 6 may be made from smooth materials including high-density polyethylene, polypropylene or glass.

Preferably, the center stage 7 is a substantially raised horizontal-plane supporting surface that is slightly lower than or equal in height to the precipice 3. Elevating center stage 7 allows the heat source 8, the carbon dioxide source 9, and/or the lure composition 10 to be isolated from contact with bed bugs and the like.

Preferably, the heat source 8 is an electric or chemical heat source that simulates or exceeds the temperature of the human body, for instance, in the range of 37 to 50 degrees Celsius (98.6 to 122 degrees Fahrenheit). Examples of electric heat sources include electrical heating pads for reptile cages and aquaria, therapeutic heat pads for human skin contact, and automobile rear-view mirror defrosters. Examples of chemical heat sources include exothermic reaction heating pads for food heating and medical compresses.

Preferably, the carbon dioxide source 9 is a compressed carbon dioxide gas or canister with a controlled release valve that emits carbon dioxide into the area circumscribed by the interior surface 4 so as to elevate the carbon dioxide level above the ambient level, for instance, between 300 p.p.m. and 1,000 p.p.m. Alternatively, any form of carbon dioxide source may be used, for example, solid carbon dioxide (i.e. dry ice) placed in an insulated mug with a small opening in a lid of the mug, or a carbonate salt combined with an aqueous acid solution. It has been shown that the carbon dioxide source 9 may emit between 2 and 1,000 ml/min of carbon dioxide while maintaining operability.

The lure composition 10 is a composition for attracting bed bugs and may comprise a combination of L-lactic acid, propionic acid, butyric acid, valeric acid, and/or octenol.

A preferred lure composition 10 comprises bed bug attracting amounts of L-lactic acid. L-lactic acid (CAS #50-21-5) is a carboxylic acid with a chemical formula of $C_3H_6O_3$. L-lactic acid has a hydroxyl group adjacent to the carboxyl group, making it an alpha hydroxy acid (AHA). In solution, L-lactic acid can lose a proton from the acidic group, producing the lactate ion $CH_3CH(OH)COO-$. L-lactic acid is chiral and has two optical isomers. One is known as L-(+)-lactic acid or (S)-lactic acid and the other, a mirror image, is D-(−)-lactic acid or (R)-lactic acid. L-(+)-Lactic acid is the biologically important isomer used in the present invention. L-lactic acid is also called (+)-Lactic acid, (+−)-2-Hydroxypropanoic acid, (+/−)-Lactic acid, (R)-2-hydroxypropanate, (R)-lactate, (RS)-2-Hydroxypropionsaeure, (S)-(+)-Lactic acid, (S)-2-Hydroxypropanoic acid, (S)-2-Hydroxypropionic acid, (S)-2-Hydroxypropionsaeure, (S)-lactate, (S)-Lactic acid, (S)-Milchsaeure, 1-Hydroxyethanecarboxylic acid, 10326-41-7, 152-36-3, 1715-99-7, 2-Hydroxy-2-methylacetic acid, 2-hydroxy-propionic acid, 2-hydroxypropanoic acid, 2-hydroxypropionic acid, 26100-51-6, 28305-25-1, 29870-99-3, 31587-11-8, 4-03-00-00633 (Beilstein Handbook Reference), 50-21-5, 598-82-3, 72-17-3, 79-33-4, 814-81-3, Acidum lacticum, Acidum sarcolacticum, Aethylidenmilchsaeure, Al3-03130, alpha-Hydroxypropanoic acid, alpha-Hydroxypropionic acid, Biolac, BRN 1720251, BRN 5238667, C01432, CCRIS 2951, CHEBI:28358, Chem-Cast, Copper lactate (ic), Copper lactate Cu(O3H5C3)2, D-LACTATE, D00111, DL-Lactic acid, DL-Milchsaeure, E 270, EINECS 200-018-0, EINECS 201-196-2, EINECS 209-954-4, EPA Pesticide Chemical Code 128929, Espiritin, Ethylidenelactic acid, FEMA No. 2611, FEMA Number 2611, Fleischmilchsaeure, HSDB 800, Indium lactate, Kyselina 2-hydroxypropanova [Czech], Kyselina mlecna [Czech], L(−)-2-Hydroxypropionsaeure, L(+)-lactate, L-(+)-alpha-Hydroxypropionic acid, l-(+)-Lactic acid, L-LACTATE, L-Lactic acid, lac, Lacolin, Lactacyd, lactasol, lactate, Lactate (TN), lactic acid, Lactic acid (7Cl,8Cl), Lactic acid (JP14/USP), Lactic acid (natural), Lactic acid monosodium salt, Lactic acid USP, Lactic acid [JAN], Lactic acid, calcium salt (2:1), L-, Lactic acid, copper (2+) salt (2:1), Lactic acid, L-, Lactic acid, monosodium salt, Lactic acid, sodium salt, Lactic acid, strontium salt (2:1), Lactovagan, LMFA01050002, LS-180647, LS-2145, Milchsaeure, Milchsaure [German], Milk acid, Monosodium lactate, NCIOpen2_000884, NSC 367919, NSC112239, NSC112240, NSC112243, NSC122003, NSC31718, NSC367919, NSC370148, NSC77164, NSC97377, Ordinary lactic acid, Paralactic acid, Paramilchsaeure, Per-glycerin, PH 90, Poly(lactic acid), Polylactic acid, Propanoic acid, 2-hydroxy-, Propanoic acid, 2-hydroxy-(9Cl), Propanoic acid, 2-hydroxy-, (+−), Propanoic acid, 2-hydroxy-, (+−)-, homopolymer, PROPANOIC ACID, 2-HYDROXY-, (.+−.)-, Propanoic acid, 2-hydroxy-, (2S)-, PROPANOIC ACID, 2-HYDROXY-, (S)-, Propanoic acid, 2-hydroxy-, (S)-(9Cl), Propanoic acid, 2-hydroxy-, calcium salt (2:1), (S)-, Propanoic acid, 2-hydroxy-, homopolymer, Propanoic acid, 2-hydroxy-, monosodium salt, Propanoic acid, 2-hydroxy-, strontium salt (2:1), Propanoic acid, 2-hydroxy-, (.+-.)-, Propel, Propionic acid, 2-hydroxy-, PURAC, Purac FCC 88, PYR, Pyruvic Acid, Racemic lactic acid, Sarcolactic acid, Sodium .alpha.-hydroxypropionate, Sodium lactate, Sodium lactate, injection, Sodium lactic acid, Strontium lactate, SY-83, Tisulac and Tonsillosan.

Preferably, the lure composition 10 comprises bed bug attracting amounts of propionic acid. Propionic acid (CAS #79-09-4) is a volatile fatty acid, $CH_3CH_2COOH$. Prepared synthetically from ethyl alcohol and carbon monoxide, propionic acid is used chiefly in the form of its propionates. Propionic acid is also called propanoic acid, metacetonic acid, methylacetic acid carboxyethane, hydroacrylic acid, ethylformic acid, ethanecarboxylic acid, $1/C3H6O2/c1-2-5-3-4/h3H,2H2$, 1H, 109-94-4, Aethylformiat, Aethylformiat [German], Al3-00407, Areginal, Carboxylic acid oxaethane, Caswell No. 443A, EINECS 203-721-0, EPA Pesticide Chemical Code 043102, Ethyl formate, Ethyl formate (natural), Ethyl formate [UN1190] [Flammable liquid], Ethyl formic ester, Ethyl methanoate, Ethyle (formiate d') [French], Ethyle (formiate d') (FRENCH), Ethylester kyseliny mravenci [Czech], Ethylformiaat, Ethylformiaat [Dutch], Etile (formiato di) [Italian], Etile (formiato di) (ITALIAN), FEMA No. 2434, FEMA Number 2434, Formic acid, ethyl ester, FORMIC ACID, ETHYL ESTER, Formic ether, HSDB 943, Mrowczan etylu, Mrowczan etylu [Polish], NSC 406578, NSC406578, NSC8828, UN1190 and ZINC01648253.

Preferably, the lure composition 10 comprises of bed bug attracting amounts of butyric acid. Butyric acid (CAS #107-92-6) is either of two colorless isomeric volatile fatty acids, $CH_3CH_2CH_2COOH$. Butyric acid is also called 1-Butyric acid, 1-propanecarboxylic acid, $1/C_4H_8O_2/c1-2-3-4(5)6/h_2-3H_2,1H_3$,(H,5,6, 107-92-6, 156-54-7, 2-butanoate, 4-02-00-00779 (Beilstein Handbook Reference), 5434-68-4, Al3-15306, AIDS-096140, AIDS096140, BEO, Bio1_000444, Bio1_000933, Bio1_001422, BRN 0906770, BUA, Butanic acid, butanoate, butanoic acid, Butanoic acid, nickel (2+) salt, Butanoic acid, sodium salt, butoic acid, Buttersaeure, Buttersaeure [German], butyrate, Butyrate sodium, Butyrate, sodium salt, Butyric acid (natural), Butyric acid [UN2820] [Corrosive], Butyric acid [UN2820] [Corrosive], Butyric acid, nickel(II) salt, Butyric acid, sodium salt, C00246, CCRIS 6552, CH3-[CH2]2-COOH, CHEBI:30772, EINECS 203-532-3, ethylacetic acid, FEMA No. 2221, FEMA Number 2221, HSDB 940, IMET 3393, Kyselina maselna [Czech], LMFA01010004, LS-443, n-Butanoic acid, n-Butyric acid, NCI60_001424, NCIMech_000707, NSC 8415, NSC174280, NSC7701, NSC8415, propylformic acid, Sodium butanoate, Sodium butyrate, Sodium n-butyrate and UN2820.

Preferably, the lure composition 10 comprises bed bug attracting amounts of valeric acid. Valeric acid (CAS #109-52-4) is a volatile fatty acid, $CH_3CH_2CH_2 CH_2COOH$. Valeric acid is also called 1-Butanecarboxylic acid, $1/C_5H_{10}O_2/c1-2-3-4-5(6)7/h2-4H_2,1H_3$,(H,6,7, 109-52-4, 12124-87-7, 19455-21-1, 4-02-00-00868 (Beilstein Handbook Reference), 42739-38-8, 5434-69-5, 556-38-7, 56767-12-5, 6106-41-8, 70268-41-6, Al3-08657, AIDS-017600, AIDS017600, BRN 0969454, Butanecarboxylic acid, C00803, CH3-[CH2]3-COOH, CHEBI:17418, EINECS 203-677-2, FEMA No. 3101, HSDB 5390, Kyselina valerova [Czech], LAEVULINIC ACID, LEA, LEVULINIC ACID, LMFA01010005, LS-3150, n-Pentanoate, n-Pentanoic acid, n-Valeric acid, NSC 406833, NSC122828, NSC406833, NSC7702, PEI, Pentanic acid, Pentanoate, Pentanoic acid, Pentanoic acid Valeric acid, Pentanoic acid, nickel (2+) salt, pentoic acid, Propylacetic acid, SHF, Valerate, Valerianic acid, Valeriansaeure, Valeric acid, VALERIC ACID, N-, Valeric acid, nickel(II) salt, Valeric acid, normal and ZINC05955167.

Preferably, the lure-composition 10 comprises bed bug attracting amounts of 1-octen-3-ol (octenol). Octenol (CAS #3391-86-4) is mushroom alcohol, with a chemical formula $C_8H_{16}O$. Octenol is also called 1-Octen-3-ol (natural), 1-Okten-3-ol [Czech], 1-Vinylhexanol, 3-Hydroxy-1-octene, 3-Octenol, 3391-86-4, 50999-79-6, Al3-28627, Amyl vinyl carbinol, Amylvinylcarbinol, BRN 1744110, EINECS 222-226-0, EPA Pesticide Chemical Code 069037, FEMA No. 2805, Matsuica alcohol, Matsutake alcohol, Matsutake alcohol [Japanese], NSC 87563, NSC87563, Oct-1-en-3-ol, Oct-1-ene-3-ol, Pentyl vinyl carbinol, and Pentylvinylcarbinol and Vinyl amyl carbine. In the present invention, R-(−)-1-octen-3-ol, which is a single isomer from the racemic mixture, is also operable. Racemic octenol (CAS #3687-48-7) is also known as EPA Pesticide Chemical Code 069038.

As stated above, the lure composition 10 comprises bed bug attracting amounts of a combination of L-lactic acid, propionic acid, butyric acid, valeric acid, and/or octenol. In particular, the lure composition 10, preferably, comprises a combination of L-lactic acid and a short chain fatty acid. The fatty acid may be taken from the group consisting of propionic acid, butyric acid and valeric acid. In addition, the lure composition 10 may also comprise octenol.

When combined in a specific ratio, the lure composition 10 has a synergistic effect. Preferably, the lure composition 10 comprises 300 parts L-lactic acid, 100 parts propionic acid, 1 part butyric acid, 1 part valeric acid, and 300 parts octenol, by weight with an acceptable variance of ±20% for each constituent.

As is well understood in the art, substitution of lure compounds may be highly desirable for effecting volatility properties. Reference to a material as a compound having a central nucleus of a stated formula may include any compound which does not alter the bond structure of the specified formula.

Compositions of the lure may comprise one or more compounds that have one or more chiral centers. Such compounds may exist and be isolated as optically active and racemic forms. Some compounds may exhibit polymorphism. It is to be understood that the present invention may encompass any racemic, optically-active, polymorphic, or stereoisomeric form, or mixtures thereof, of a compound of the invention, that possesses the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) or using other tests which are well known in the art.

The lure composition may be provided in any of a number of forms, solutions or carriers. For example, the use of L-lactic acid, propionic acid, butyric acid or valeric acid salts may be appropriate. Acceptable salts may be obtained using standard procedures well known in the art. Alkali metal (for example, sodium, potassium or lithium) or alkaline earth metal (for example, calcium) salts of carboxylic acids can be made.

The lure composition 10 may be suspended in an aqueous solution, a gel matrix, a solid or a compressed gas form, as well.

The lure composition 10 formulations may be placed in any suitable container or device for dispensing the attractant compound and attracting or trapping bed bugs. For example, the formulations can be placed in a suitable device so that one can obtain evaporation of the attractant compound from a porous medium or wax-like medium containing the attractant compound positioned within the dispensing device.

As another alternative, the attractant lure composition 10 may be employed in any formulation suitable for dispensing effective amounts of attractant compounds. The compounds will generally be employed in formulations comprising a carrier containing the attractant compounds. An example of a suitable carrier is a gel matrix material which can be a hydrolyzed protein gel material such as gelatin or a polysaccharide gel as disclosed by Williams in U.S. Pat. No. 6,790,436 in 2004.

Another example carrier is a cooled paraffin wax and octenol solution mixed with salts of L-lactic acid, proprionic acid, butyric acid, and/or valeric acid. The attractant lure compounds may also be volatized from the liquid state directly from a wicking material with release rates controlled by head space and orifice size of a container.

In the lure arrangement 11 of FIGS. 1-4 comprised by a combination of the heat source 8, the carbon dioxide source 9 and the lure compound 10, each element is capable of attracting bed bugs and the like when provided at the appropriate levels of emission; however, the combination of a lure composition 10 in a heated and carbon dioxide rich environment results in an accentuated synergistic effect. Preferably, the heat source 8 generates heat in the range of 37 to 50 degrees Celsius (98.6 to 122 degrees Fahrenheit). Preferably, the carbon dioxide source 9 emits approximately in the range of 2 to 1,000 ml/min of carbon dioxide. And, preferably, the lure composition 10 comprises a combination of 300 parts L-lactic acid, fatty acids including 100 parts propionic acid, 1 part butyric acid, and 1 part valeric acid, and 300 parts octenol, by weight with an acceptable variance of ±20%.

A method of using the pitfall trap 1 for attracting and capturing bed bugs and the like comprises the step of positioning a pitfall trap 1 in an environment suspected or known to be infested by bed bugs or the like. For example, the trap 1 may be placed on the floor in a bedroom known to be infested with bed bugs near or under a bed. The trap may be constructed with a central well in which the leg of a bed is set to capture bed bugs as they travel to or from the bed. Bed bugs are known, for example, to leave a bed during daylight hours only to return at night. The trap 1 may also be placed on the floor of a cargo bay or passenger cabin of a ship or airplane suspected of containing bed bugs. The climb-up pitfall trap 1 is loaded with the sensory lures comprised by the heat source 8, the carbon dioxide source 9 and the lure composition 10, as described above. The sensory lures are activated thereby exposing the environment to heat from the heat source 8, carbon dioxide from the carbon dioxide source 9 and gaseous vapors from the lure composition 10. Bed bugs and the like will, then, be attracted towards the pitfall trap 1 and captured therein upon crossing the precipice 3 and becoming detained by the smooth interior surface 4 in the receptacle 5. The contained bug can then be disposed of in any number of ways.

Figure 5:
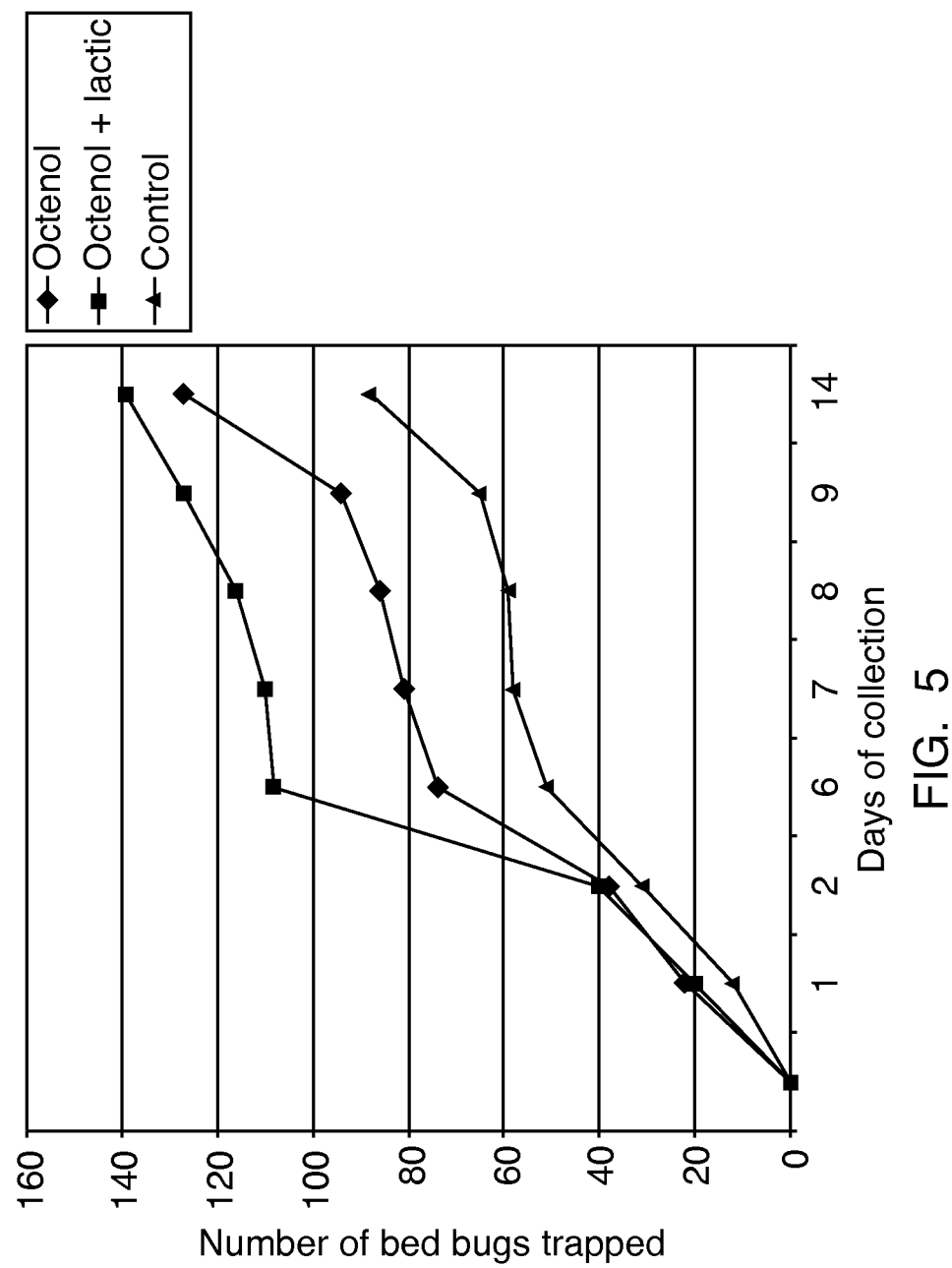
FIG. 5 is a chronological showing of bed bugs captured in the climb-up pitfall trap of the present invention with various sensory lures.
Figure 6:
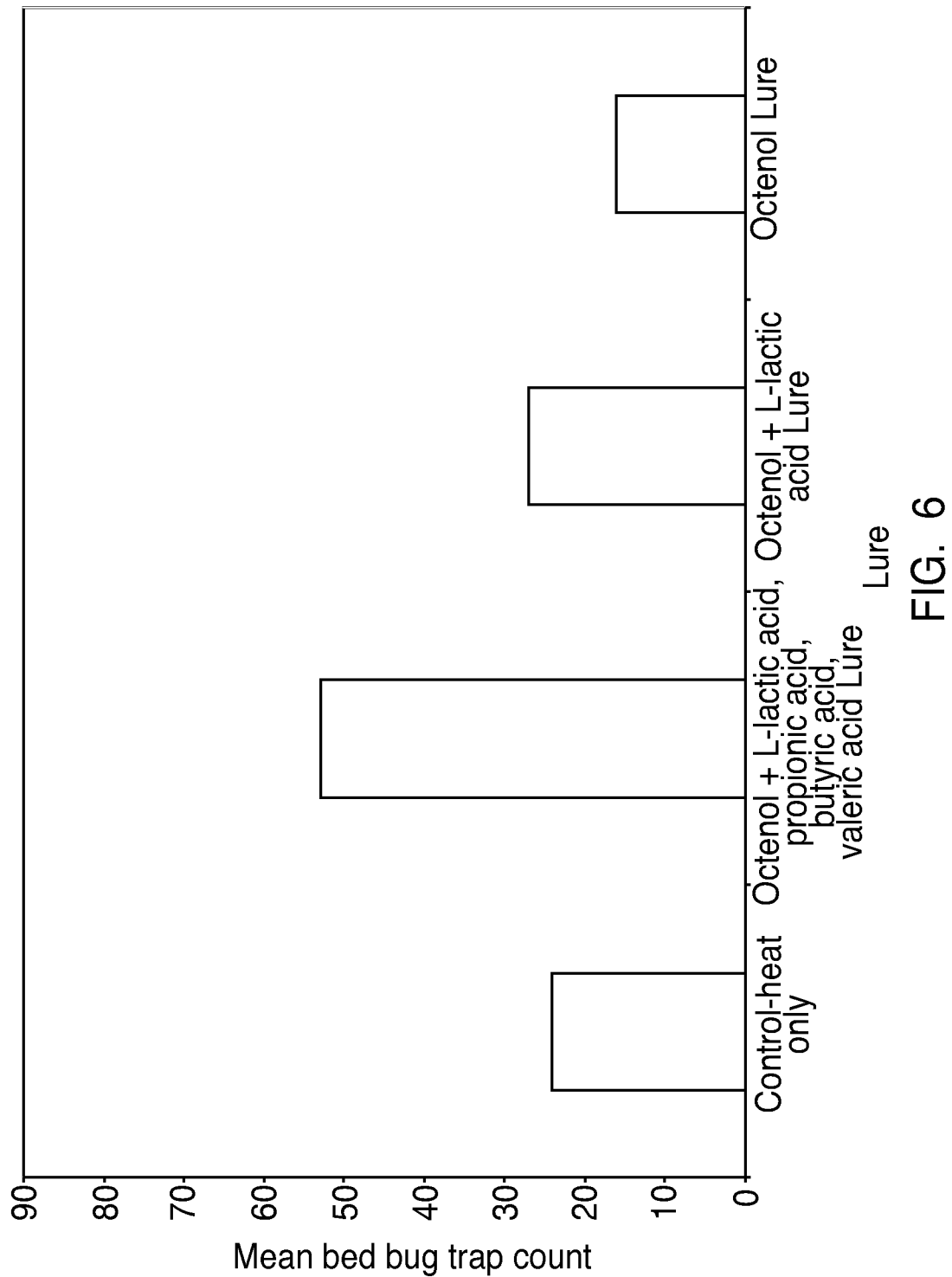
FIG. 6 is a bar graph showing the number of bed bugs captured in one test of the climb-up pitfall trap of the present invention with various sensory lures.
Figure 7:
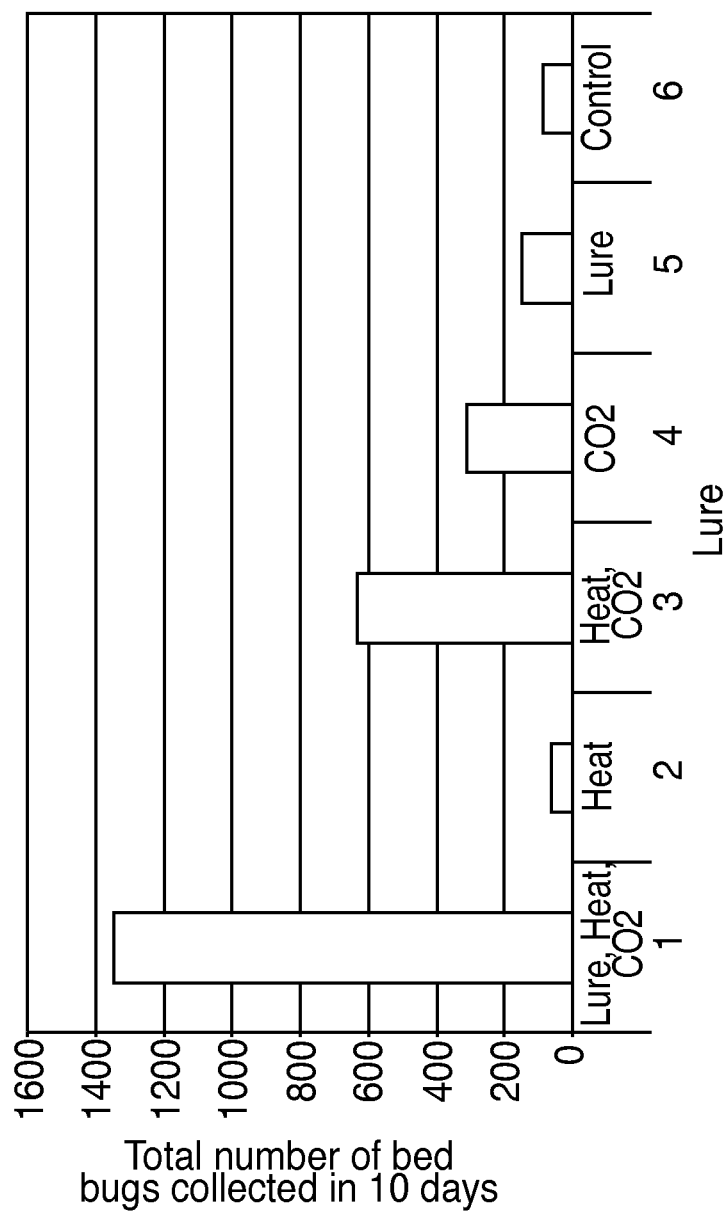
FIG. 7 is a bar graph showing the number of bed bugs captured in another test of the climb-up pitfall trap with various sensory lures.

Referring to FIGS. 5-7, the relative efficacy of the method implementing an assortment of sensory lures is shown. FIGS. 5-7 will be discussed in reference to the following examples.

EXAMPLE 1

A molded polypropylene dog dish was turned upside down to form a climb-up pitfall trap 1 as shown in FIG. 1. The exterior surface 2 was covered with cloth, the cloth being attached by masking tape, to form a climbing surface. Precipice 3 was formed by the outer edge of the dog dish. Interior surface 4 was formed by the underside of the outer rim of the dog dish which faces upward when the dog dish is turned upside down. Receptacle 5 was formed along the inside of the precipice 3 by the interior surface 4 and the retaining surface 6, effectively forming a capture moat area. The retaining surface 6 was formed by the underside of the inner bowl walls of the dog dish. Center stage 7 was formed by the underside of the bowl portions of the dog dish.

The trap 1 was positioned on the floor of an apartment building known to be infested by bed bugs.

Referring to the chronological chart of FIG. 5, the trap 1 was initially loaded with a heat blanket (heat source 8) alone. The heat blanket generated temperatures of 44.8 to 47.3 degrees Celsius (112.6 to 117.1 degrees Fahrenheit). The trap 1 with heat source 8 was tested for 14 days. This served as the control test as indicated in FIG. 5.

The trap 1 was then loaded with an octenol lure in addition to the heat source 8, but excluding lactic acid. The heat blanket again generated heat. The trap 1 with heat source 8 and octenol lure was tested for 14 days with the results shown in FIG. 5.

The trap 1 was then loaded with an octenol and L-lactic acid lure as described above, in place of the octenol lure. The heat blanket again generated heat. The trap 1 with heat source 8 and octenol and L-lactic acid lure was tested for 14 days with the results shown in FIG. 5.

All traps caught bed bugs, as shown in FIG. 5. However, both the trap with the heat and octenol lure and the trap with the heat and octenol and L-lactic acid lure caught more bugs than the trap in the control test (trap with heat source alone). The trap with the octenol and L-lactic acid lure caught the most bugs and showed a significantly more effective capture rate after two days of collection.

EXAMPLE 2

Experimental Lure Composition

A molded polypropylene dog dish was turned upside down to form climb-up pitfall trap 1 as described in Example 1. The exterior surface 2 was covered with Pellon® featherweight fusible interfacing to form a climbing surface. The surface of the receptacle 5 had a satin finish and was measured using a Mahr Federal Pocket Surf III probe to reveal a surface roughness of 33 to 96 microinch.

The trap 1 was positioned on the floor of an apartment building known to be infested by bed bugs.

As indicated in the bar chart of FIG. 6, the trap 1 was loaded with a heat blanket (heat source 8). The heat blanket generated temperatures of 44.8 to 47.3 degrees Celsius (112.6 to 117.1 degrees Fahrenheit). The trap with heat source 8 was tested several times for 14 days with a modest mean trap count. This test served as a control test.

The trap was then loaded with an octenol lure without L-lactic acid. The heat blanket again generated heat. The trap with heat source 8 and octenol lure was tested several times for 14 days with less effective results than heat alone.

The trap was then loaded with an octenol and L-lactic acid lure, in place of the octenol lure. The heat blanket again generated heat. The trap with heat source 8 and octenol and L-lactic acid lure was tested several times for 14 days and showed a mean trap count greater than heat or octenol alone.

The trap was then loaded with an experimental lure consisting of a combination of 100 micrograms of L-lactic acid, 33 micrograms of propionic acid, 0.33 micrograms of butyric acid, 0.33 micrograms of valeric acid and 100 micrograms of octenol (lure composition 10), the experimental lure being combined in a fragrance releasing gel. The heat blanket again generated heat. The trap with heat source 8 and the experimental lure (lure composition 10) was tested several times for 14 days, and on average caught two (2) times as many bed bugs as the other traps.

EXAMPLE 3

Carbon Dioxide Synergism With Experimental Lure Composition

A molded polypropylene dog dish was turned upside down to form the climb-up pitfall trap 1 as described in Example 2.

The trap 1 was positioned on the floor of an apartment building known to be infested by bed bugs, and was tested without any lure. This served as the control test illustrated as Test 6 in FIG. 7.

The trap was loaded with a heat blanket (heat source 8). The heat blanket generated temperatures of 44.8 to 47.3 degrees Celsius (112.6 to 117.1 degrees Fahrenheit). The trap 1 with heat source 8 was tested with results shown as Test 2 in FIG. 7.

The trap was then loaded with a flexible tube connected to a 5 lbs. compressed carbon dioxide cylinder (carbon dioxide source 9). The carbon cylinder emitted 500 ml/min of carbon dioxide through a tube to the area over the center stage 7 of the trap. The trap with carbon dioxide source 9 was tested with the results shown as Test 4 in FIG. 7.

The trap was then loaded with an experimental lure comprising: 100 micrograms of L-lactic acid, 33 micrograms of propionic acid, 0.33 micrograms of butyric acid, 0.33 micrograms of valeric acid and 100 micrograms of octenol (i.e., "lure composition 10"), the experimental lure being combined in a fragrance releasing gel. The trap with experimental lure (lure composition 10) was tested with the results indicated in Test 5 of FIG. 7.

The trap was then loaded with the heat blanket and the carbon dioxide cylinder. The trap with heat source 8 and carbon dioxide source 9 was then tested with the results indicated in Test 3 of FIG. 7.

The trap was then loaded with the heat blanket, the carbon dioxide source, and the experimental lure of test 5. The trap with heat source 8, carbon source 9 and experimental lure (lure composition 10) was then tested with the results indicated in Test 1 of FIG. 7.

Each trap arrangement in FIG. 7 was tested for 14-days. All traps caught bed bugs.

As indicated in FIG. 7, there was no significant difference between the trap with the heat source 8 and the control test (trap only). The trap with lure composition 10 caught approximately two (2) times the number of bed bugs as the control test (trap only). The trap with carbon dioxide source 9 caught approximately three (3) times the number of bed bugs as the control (trap only). The trap with heat source 8 and carbon dioxide source 9 caught approximately four (4) times the number of bed bugs as the control test (trap only). And the trap with heat source 8, carbon dioxide source 9 and lure composition 10 caught more than ten (10) times the number of bed bugs as the control test, and over twice (2) the number of bed bugs of the next best trap (heat and carbon dioxide).

As indicated by the results shown in FIG. 7, a synergistic effect was observed with the combination of heat source 8, carbon dioxide source 9 and lure composition 10.

It should be understood that the foregoing description is only illustrative of the invention. Various alternatives and modifications can be devised by those skilled in the art without departing from the broader aspects of the present invention.

What is claimed is:

1. A climbable pitfall trap for bed bugs and the like, the trap comprising:
   a rough exterior surface sloping upwardly and outwardly from a bottom of the exterior surface to a to of the exterior surface, the exterior surface serving as a climbing wall, which extends continuously around an outside of the trap and defines an edge at the to of the exterior surface, wherein the exterior surface is climbable by crawling arthropods with hooked tarsal claws;
   a precipice lining the edge of the exterior surface;
   a smooth interior surface connected to the precipice and sloping downward and inward from the precipice to form a first pitfall, the smooth interior surface having a surface roughness preventing bed bugs and the like passing over the precipice from resisting a fall down into the trap and from climbing up the interior surface to escape from the trap; and
   a smooth sloped retaining surface located inwardly of and opposed to the interior surface and forming a second pitfall;
   wherein the interior surface defines an outer portion of a receptacle and the opposed retaining surface defines an inner portion of the receptacle.

2. The climbable pitfall trap of claim 1,
   wherein the exterior surface has a surface roughness of more than 300 microinch.

3. The climbable pitfall trap of claim 1,
   wherein a roughness of the exterior surface is established by a coating applied to the exterior surface.

4. The climbable pitfall trap of claim 1,
   wherein a roughness of the exterior surface is established by a material applied to the exterior surface.

5. The climbable pitfall trap of claim 4,
   wherein the material is selected from the group consisting of: a fabric, paper and coarse abrasive.

6. The climbable pitfall trap of claim 1,
   wherein the exterior surface is made of or coated by unfinished wood or roughed plastic.

7. A trap for capturing bed bugs and the like comprising:
   a sloped exterior climbing wall, which extends around a periphery of the trap so as to be encountered by bed bugs and the like approaching the trap from any direction, the climbing wall having a top and bottom and a surface roughness between the top and bottom enabling bed bugs and the like to climb up the wall using their tarsal claws, the exterior climbing wall sloped upwardly and outwardly from the bottom to the top;
   an interior wall extending around the periphery of the trap and located inside the exterior wall, the interior wall being connected to the top of the exterior wall to form a precipice, the interior wall sloping downwardly and inwardly from the precipice, and having a steepness and a surface roughness preventing bed bugs and the like passing over the precipice from resisting a fall down into the trap and from climbing up the interior wall to escape from the trap;
   a smooth sloped retaining wall located inwardly of and connected with the interior wall to form a receptacle extending around the periphery of the trap, the retaining wall having a steepness and a surface roughness preventing bed bugs and the like from climbing up the retaining wall to escape from the trap.

8. A trap for capturing bed bugs and the like as defined in claim 7 wherein the surface roughness of the exterior wall is greater than 300 microinches.

9. The trap for capturing bed bugs and the like as defined in claim 7 wherein the surface roughness of the interior wall is less than 100 microinches.

10. The trap for capturing bed bugs and the like as defined in claim 7 wherein the surface roughness of the climbing wall is provided by a material secured to the climbing wall.

11. The trap for capturing bed bugs and the like as defined in claim 7 wherein the surface roughness of the interior wall is obtained by forming the interior wall from a smooth material selected from the group of materials consisting of high density polyethylene, polypropylene, and glass.

12. A climbable pitfall trap for bed bugs and the like, the trap comprising:
 a rough exterior surface, which extends around a periphery of the trap and defines an edge at a top of the exterior surface, and the exterior surface sloping upwardly and outwardly from a bottom of the exterior surface to the to of the exterior surface, the exterior surface serving as a climbing wall, a roughness of the exterior surface enabling bed bugs to climb the exterior surface using their tarsal claws and reach the edge;
 a precipice lining the edge of the exterior surface;
 a smooth interior surface connected to the precipice and sloping downwardly and inwardly from the precipice to form a first pitfall, a smoothness of the interior surface rendering the bed bugs and the like incapable of climbing up the interior surface to the precipice; and
 a smooth sloping retaining surface located inwardly of the interior surface, a smoothness of the retaining surface rendering bed bugs incapable of climbing the retaining surface; wherein:
 the interior surface and the sloping retaining surface are connected to form a receptacle extending around the periphery of the trap; and
 the receptacle lies between the interior surface and the retaining surface and serves as a repository for captured bed bugs and the like.

13. The trap of claim 12, further comprising:
 a center stage connected to an upper part of the retaining surface.

14. The trap of claim 12, further comprising:
 at least one attractant or lure provided in an area surrounded by the interior surface.

15. The trap of claim 12,
 wherein the exterior surface has a surface roughness of more than 300 microinch.

16. The trap of claim 12,
 wherein the interior surface has a surface roughness of less than 100 microinch.

17. The trap of claim 12,
 wherein the retaining surface has a surface roughness of less than 100 microinch.

18. A climbable pitfall trap for bed bugs and the like, the trap comprising:
 a rough exterior surface, which extends around a periphery of the trap and defines an edge at a top of the exterior surface, and the exterior surface sloping upwardly and outwardly from a bottom of the exterior surface to the to of the exterior surface, the exterior surface serving as a climbing wall for bed bugs and the like;
 a precipice lining the edge of the exterior surface;
 a smooth interior surface connected to the precipice inwardly of the exterior surface and sloping downwardly and inwardly from the precipice to a lower edge of the smooth interior surface to form a first pitfall extending around the trap that is not climbable by bed bugs and the like;
 a smooth sloped retaining surface located inwardly of the interior surface and connected to the lower edge of the interior surface to form a receptacle extending around the trap, wherein the retaining surface defines a second pitfall that is not climbable by bed bugs and the like; and
 a lure composition provided within an area surrounded by the interior surface and comprising a combination of:
  (a) L-lactic acid; and
  (b) a fatty acid selected from the group consisting of:
   (1) proprionic acid,
   (2) butyric acid, and
   (3) valeric acid.

19. The trap of claim 18, further comprising:
 a heat source and a carbon dioxide source provided within an area surrounded by the interior surface.

20. The trap of claim 19,
 wherein the heat source produces heat in the range of 37 to 50 degrees Celsius.

21. The trap of claim 19,
 wherein the carbon dioxide source emits carbon dioxide in the range of 2 to 1,000 ml/min.

22. The trap of claim 18,
 wherein the lure composition further comprises:
 (c) octenol.

23. The trap of claim 18,
 wherein the lure composition comprises the combination of:
 (a) 300 parts L-lactic acid, and
 (b) the fatty acid selected from the group consisting of:
  (1) 100 parts propionic acid,
  (2) 1 part butyric acid, and
  (3) 1 part valeric acid,
 by weight with an acceptable variance of ±20%.

24. The trap of claim 23,
 wherein the lure composition further comprises:
 (c) 300 parts octenol,
 by weight with an acceptable variance of ±20%.

25. The trap of claim 18, wherein the exterior surface has a surface roughness of more than 300 microinch.

26. The trap of claim 18, wherein the interior surface has a surface roughness of less than 100 microinch.

27. The trap of claim 18, further comprising:
 a center stage connected to an upper part of the retaining surface, wherein the center stage defines an area that is isolated from captured bed bugs and the like.

\* \* \* \* \*

UNITED STATES PATENT AND TRADEMARK OFFICE
CERTIFICATE OF CORRECTION

PATENT NO. : 8,966,812 B2  
APPLICATION NO. : 12/327856  
DATED : March 3, 2015  
INVENTOR(S) : Susan McKnight Page 1 of 1

It is certified that error appears in the above-identified patent and that said Letters Patent is hereby corrected as shown below:

In the Claims

Column 12, line 9 – after "an edge at the" change "to" to "top".

Column 13, line 17 – after "of the exterior surface to the" change "to" to "top".

Column 14, line 1 – after "of the exterior surface to the" change "to" to "top".

Signed and Sealed this  
Seventh Day of July, 2015

Michelle K. Lee  
*Director of the United States Patent and Trademark Office*